United States Patent [19]

Kresse

[11] Patent Number: 4,894,855
[45] Date of Patent: Jan. 16, 1990

[54] X-RAY DIAGNOSTICS SYSTEM HAVING SUSPENDED POSITION ADJUSTABLE COMPONENTS

[75] Inventor: Heinz Kresse, Uttenreuth, Fed. Rep. of Germany

[73] Assignee: Siemens Aktiengesellschaft, Berlin and Munich, Fed. Rep. of Germany

[21] Appl. No.: 289,429

[22] Filed: Dec. 23, 1988

Related U.S. Application Data

[63] Continuation of Ser. No. 912,041, Sep. 26, 1986, abandoned.

[30] Foreign Application Priority Data

Oct. 9, 1985 [DE] Fed. Rep. of Germany ....... 3536079

[51] Int. Cl.⁴ ............................................. H05G 1/02
[52] U.S. Cl. ................................. 378/196; 378/189
[58] Field of Search ............. 378/23, 147, 195–198, 378/208–209

[56] References Cited

U.S. PATENT DOCUMENTS

| | | | |
|---|---|---|---|
| 3,025,401 | 3/1962 | Lauterbach | 378/197 |
| 3,644,735 | 2/1972 | Vanderveldon | 378/197 |
| 3,714,427 | 1/1973 | Reiniger et al. | 378/197 |
| 3,720,817 | 3/1973 | Dinwiddie | 364/414 |
| 3,777,124 | 12/1973 | Pavkovich | 364/414 |
| 3,783,251 | 1/1974 | Pavkovich | 378/196 |
| 4,087,694 | 5/1978 | Hellstrom et al. | 378/195 |
| 4,101,774 | 7/1978 | Elzinga et al. | 378/25 |
| 4,298,801 | 11/1981 | Heitman et al. | 378/196 |
| 4,323,758 | 4/1982 | Vokurka | 219/125.1 |
| 4,334,155 | 6/1982 | Gieschen et al. | 378/196 |
| 4,426,725 | 1/1984 | Grady | 378/196 |
| 4,435,830 | 3/1984 | Suzuki et al. | 378/197 |
| 4,481,657 | 11/1984 | Larsson | 378/209 |
| 4,490,835 | 12/1984 | Wons | 378/147 |
| 4,501,011 | 2/1985 | Hanck et al. | 378/197 |
| 4,541,293 | 9/1985 | Caugant et al. | 378/197 |

FOREIGN PATENT DOCUMENTS

| | | |
|---|---|---|
| 0073185 | 3/1983 | European Pat. Off. . |
| 3218301 | 11/1983 | Fed. Rep. of Germany . |
| 2225911 | 11/1974 | France . |
| 2406426 | 5/1979 | France . |

OTHER PUBLICATIONS

"Off-line-Kollisionskontrolle bei Industrieobotern", by Scholing et al. VDI Zeitschrift 125, #17, 9-1983, pp. 647-652.

Primary Examiner—Craig E. Church
Assistant Examiner—John C. Freeman
Attorney, Agent, or Firm—Hill, Van Santen, Steadman & Simpson

[57] ABSTRACT

An x-ray diagnostics system has a number of sub-systems, including an x-ray generating system, an image pick-up system, and a patient support system. At least two of these sub-systems have components thereof which are individually suspended by support mechanisms which permit three-dimension movement and adjustment of the component by a motor. The motor is connected to a central computer which controls the motion and positioning of all components for moving the components to selected positions relative to a patient and relative to each other.

8 Claims, 1 Drawing Sheet

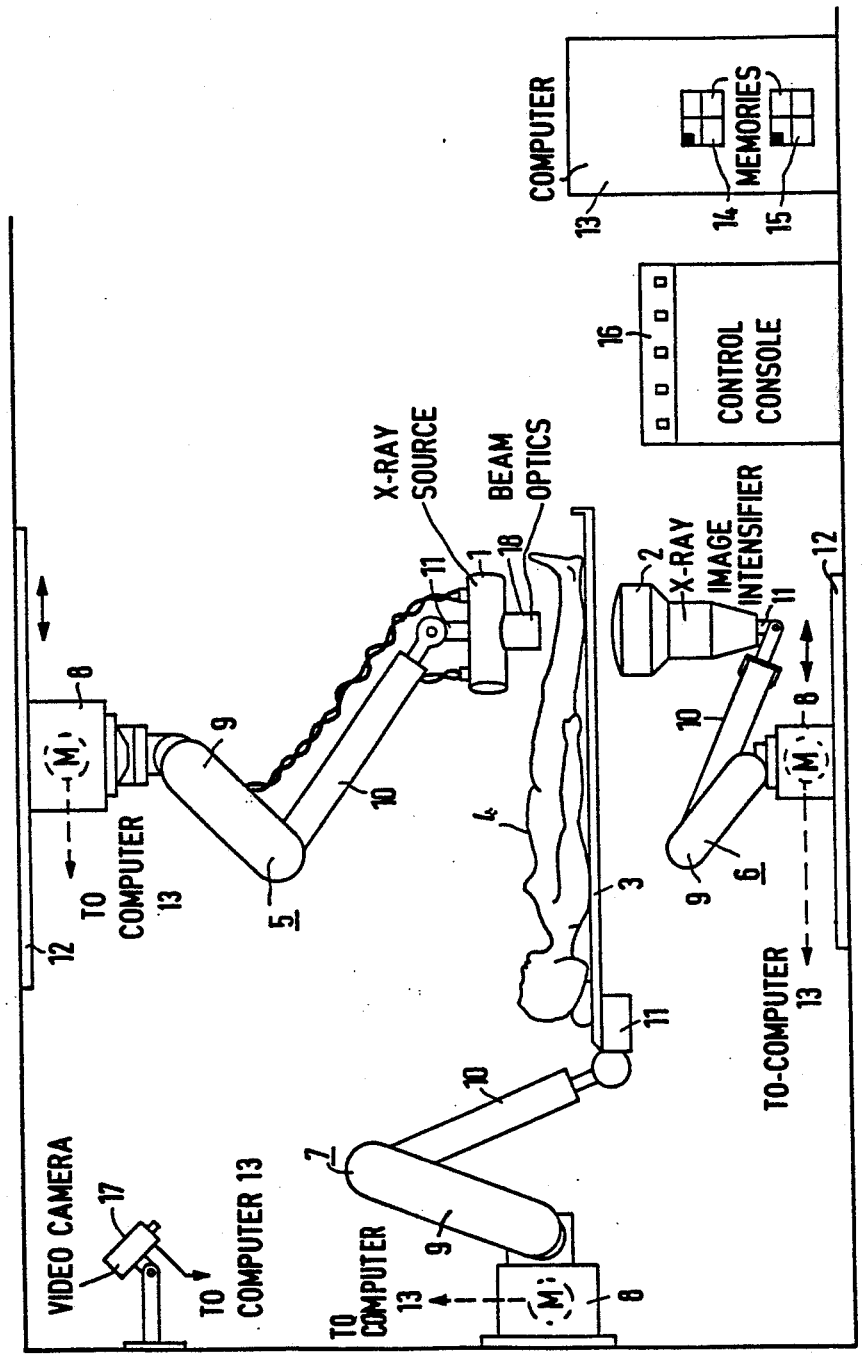

X-RAY DIAGNOSTICS SYSTEM HAVING SUSPENDED POSITION ADJUSTABLE COMPONENTS

This is a continuation of application Ser. No. 912,041 filed Sept. 26, 1986, abandoned.

BACKGROUND OF THE INVENTION

1. Field of the Invention

The present invention relates to an x-ray diagnostics system including an x-ray generating system, an image pick-up system and a patient support system, and in particular to such a diagnostics system including individually adjustable support means for each of the sub-systems operated by a central computer.

2. Description of the Prior Art

An x-ray diagnostics system is described in German OS No. 32 18 301 which includes a feedback control device for adjusting the positions of the x-ray tube and the radiation receiver. For this purpose, two columns are displaceably attached to a carrier connected to the ceiling of the examination room. An x-ray tube and an x-ray image intensifier are respectively carried at the free ends of these columns. The length of the columns can be varied, so that the height of the x-ray tube and the x-ray image intensifier can be adjusted. The x-ray tube and the image intensifier may also be pivoted around the axis of a column. A feedback control device is provided so that the image intensifier is always aligned to the x-ray tube so that the x-ray beam strikes the radiation-sensitive surface thereof. The feedback control device effects an electrical coupling of the two components. This system has a disadvantage in that, as a consequence of the rigid columns, not all desired exposure positions can be achieved without the use of further mechanical structural components, so that such a system cannot be universally employed.

SUMMARY OF THE INVENTION

It is an object of the present invention to provide an x-ray diagnostics system having a plurality of sub-systems with a means for individually mounting each of the components of the sub-systems with free mobility so that the system can be universally employed in any configuration.

The above object is achieved in accordance with the principles of the present invention in an x-ray diagnostics system wherein at least two components of different sub-systems are individually suspended so as to be moveable in three dimensions by a motor-actuateable adjustment means. A central computer is connected to the adjustment means for selecting the positions of the components. Substantially all possible positions of the system components can be arbitrarily selected, and the computer can further maintain alignment of system components relative to each other so that mechanical structural elements connecting components in different sub-systems are not necessary.

Free accessibility to the patient during an examination is achieved in the diagnostics system disclosed herein in an embodiment wherein the adjustment means are robot arms each having a first lever rotationally and pivotally attached to a support location. A free end of the first lever is pivotally connected to a second lever, which is rotationally and pivotably attached to the supported system component. The support location to which the first lever is attached is connected to a motor for operating the robot arm. Because of the small mass of the robot arms to be moved, hold positions can be reached faster, and the carrying arms occupy less space in these hold positions. Various positions identified before an examination can be easily recalled in an embodiment wherein the computer includes a storage means for various fixed positions, which can be entered by a program.

The computer memory can also be used to store a number of different program sequences for directing continuous movement of system components in accordance with a selected function. Tomographic exposures can be executed with the system disclosed herein by using a stored program which moves the x-ray tube and the image pick-up system oppositely relative to each other in two respective planes which are parallel. Simple computer tomography exposures can be undertaken by using a program wherein the x-ray tube and the image pick-up system are moved along a circular path around a common center, with the x-ray tube being provided with a radiation diaphragm for emitting a fan-shaped x-ray beam. Rotational semicircular movements of the patient can also be achieved by providing a similar suspension means for the patient support bed, also operated by a motor connected to the computer. Other patient movement, such as back and forth movements in a lateral plane, and up and down movements, can also be achieved by a suitable program.

One or more of the support means, consisting of the motor, the motor housing, and two levers, can be mounted on a rail connected to the floor or ceiling of the examination room permitting lateral movement of the support means and thus further expanding the adjustment capability of the system. Additionally, at least one television camera can be mounted so as to be directed at the examination area as a safety device for the freely moveable system components. The television camera is connected to the computer and the signal from the camera is utilized to prevent movement of the components to positions at which articles or persons recognized by the television camera are situated.

DESCRIPTION OF THE DRAWING

The single figure shows a side view of an examination room in which an x-ray diagnostics system constructed in accordance with the principles of the present invention is arranged.

DESCRIPTION OF THE PREFERRED EMBODIMENTS

An x-ray diagnostics system constructed in accordance with the principles of the present invention is shown in the figure, the system including an x-ray tube 1, an x-ray image intensifier 2 functioning as an image pick-up system, and a patient support bed 3 supporting an examination subject 4. The system components 1, 2 and 3 are respectively suspended by individual supporting means 5, 6 and 7. The supporting means 5, 6 and 7 are each individually adjustable and are constructued as robot arms.

Each support means 5, 6 and 7 includes a base 8, containing a motor M for moving the robot arm, connected either to the wall, ceiling or floor of the examination room. Each supporting means 5, 6 and 7 also includes a first lever connected to the base 8 in a manner permitting rotational and pivotable movement driven by the motor M. Each supporting means 5, 6 and 7 also includes a second lever 10, connected to the free end of the first lever 9, which can also be pivoted by the motor M. The second lever 10 is also connected by means permitting motor-actuable articulation. The free end of the second lever 10 is connected to one of the aforementioned components via a mount 11. The mount 11 permits rotational and pivotal movement of the component mounted thereon with respect to the free end of the second lever 10.

In order to further expand the range of movement of the system components 1, 2 and 3, one or more of the bases can be mounted on rails 12 so as to be laterally displaceable thereon, as shown for the support means 5 for the x-ray tube 1 and the support means 6 for the x-ray image intensifier 2.

The respective motors M for the support means 5, 6 and 7 are connected to a central computer 13 functioning as the main control device for the system. The computer 13 includes memories 14 and 15 in which various fixed positions are stored as well as different program sequences for controlling continuous movement of the system components. The various programs, positions or functions can be recalled by means of a control console 16 connected to the computer 13. Various positions, identified with a light sighting device before an x-ray exposure, can be entered into the memory 14, for example, these positions being capable of being recalled later during the examination in response to depression of a key on the console 16. The distances of the system components 1, 2 and 3 relative to each other can be recalled from the memory 14 by depression of a key on the console 16, thus permitting the magnification factor and the image sharpness to be controlled. Instead of the control console 16, it is alternatively possible to provide a voice input control means for operating the system components 1, 2 and 3.

Several different motion sequences for the system components 1, 2 and 3 can be stored in the program memory 15. One such program may, for example, control oppositely directed movement of the x-ray tube 1 and the x-ray image intensifier 2 in two respective parallel planes along a linear or circular path for making an exposure of a selected slice of the examination subject. Computer tomograph exposures of a slice can also be produced using a program stored in the memory 15 which controls the support means 5 and 6 such that the x-ray tube 1 and the x-ray image intensifier 2 are moved circularly around the longitudinal axis of the patient as a common center. For this purpose, beam optics 18, such as a primary radiation diaphragm, connected to the x-ray tube 1 are adjusted so as to emit a fan-shaped x-ray beam which is received by the x-ray image intensifier 2 or by another suitable radiation receiver. The output signals of the x-ray image intensifier 2 are supplied to the computer 13, which calculates a computer tomograph image from the signals associated with the various positions.

The position of the patient support bed 3 can be adjusted by movement of the support means 7 based on another program stored in the memory 15. Such movement may, for example, include semicircular rotational movement about the longitudinal axis of the patient, vertical and lateral movement of the patient support bed 3, or positioning of the patient support bed 3 to effect transfer of the patient from a transport device to the patient support bed 3. Movement of the examination subject 4 on the patient support bed 3 can be coordinated with movement of the x-ray source 1 and the image intensifier 2 by simultaneously operating all of the support means 5, 6 and 7. It is possible, however, to utilize a conventional column support for the patient bed 3, instead of the support means 7, because for many installations the free mobility of the x-ray tube 1 and the x-ray image intensifier 2 provided by the support means 5 and 6 will be sufficient.

In order to avoid risk of injury to patients, operating personnel, and the components of the diagnostics system which may be caused by moving component parts, each moveable component may be equipped with optical, tactile or ultrasonic sensors in a known manner. It is also possible, however, to employ one or more video cameras 17 connected to the computer 13 which acquire the contours of persons and articles within the field of view. These signals are supplied to the computer 13 and, after suitable image processing, can be utilized to block movement of the components to those spatial positions which are occupied by persons or articles recognized by the camera 17.

Although modifications and changes may be suggested by those skilled in the art it is the intention of the inventor to embody within the patent warranted hereon all changes and modifications as reasonably and properly come within the scope of his contribution to the art.

What is claimed is:

1. An x-ray diagnostics system comprising:
an x-ray source;
a patient support bed;
an x-radiation receiver for detecting radiation passing through an examination subject on said patent support bed;
means for suspending said x-ray source including a base, a first lever having a first end connected to said base so as to be swivelable about a first axis, and a second end, a second lever having a first end connected to said second end of said first lever so as to be swivelable about a second axis, said first and second axes being parallel, and a second end connected to said x-ray source, said base containing a motor for operating said means for suspending said x-ray source;
means for suspending said patient support bed including a base, a first lever having a first end connected to said base so as to be swivelable about a first axis, and a second end, a second lever having a first end connected to said second end of said first lever so as to be swivelable about a second axis, said first and second axes being parallel, and a second end connected to said patient support bed, said base containing a motor for operating said means for suspending said patient support bed;
means for suspending said x-radiation receiver including a base, a first lever having a first end connected to said base so as to be swivelable about a first axis, and a second end, a second lever having a first end connected to said second end of said first lever so as to be swivelable about a second axis, said first and second axes being parallel, and a second end connected to said x-radiation receiver, said base containing a motor for operating said means for suspending said x-radiation receiver;
said means for suspending said x-ray source, said means for suspending said patient support bed and said means for suspending said x-radiation receiver all being disposed separately from each other; and
a computer connected to said means for suspending said x-ray source, to said means for suspending said patient support bed and to said means for suspending said x-radiation receiver for controlling and coordinating movement of said x-ray source, said x-radiation receiver and said patient support bed, said computer including a programmable memory containing a plurality of different program sequences for simultaneously moving said x-ray source, said patient support bed and said x-radiation receiver along predetermined paths.

2. An x-ray diagnostics system as claimed in claim 1, wherein said x-ray source, said patient support bed and said x-radiation receiver are defined as supported components, and wherein each second lever further comprises means connecting said second lever to one of said supported components for permitting rotational and pivotable movement of said one component with respect to said second lever.

3. An x-ray diagnostics system as claimd in claim 1, wherein said computer includes a programmable memory for storing a plurality of fixed positions at least for said x-ray source and said x-radiation receiver.

4. An x-ray diagnostics system as claimed in claim 1, wherein said computer includes a programmable memory for storing at least a program for moving said x-ray source and said x-radiation receiver in opposite directions relative to each other in two respective parallel planes.

5. An x-ray diagnostics system as claimed in claim 1, wherein said computer includes a programmable memory for storing a program for moving said x-ray source and said x-radiation receiver along a circular path around a common center.

6. An x-ray diagnostics system as claimed in claim 5, further comprising a radiation diaphragm attached to said x-ray source for generating a fan-shaped x-ray beam.

7. An x-ray diagnostics system as claimed in claim 1, further comprising:
at least one rail for supporting at least one of said means for suspending said x-ray source or said means for suspending said x-radiation receiver for permitting lateral movement thereof along said rail.

8. An x-ray diagnostics system as claimed in claim 1, further comprising at least one video camera having a field view encompassing said x-ray source, said patient support bed and said x-radiation receiver for supplying a signel to said computer identifying selected articles or personnel in said field view, and wherein said computer blocks movement of at least said x-ray source and said x-radiation receiver to positions occupied by said articles or personnel.

* * * * *